United States Patent [19]

Ohtaka et al.

[11] Patent Number: 4,742,062
[45] Date of Patent: May 3, 1988

[54] BENZYLPIPERAZINE COMPOUND AND PHARMACEUTICAL COMPOSITION AS HYPOLIPIDEMIC AGENT

[75] Inventors: Hiroshi Ohtaka, Osaka; Yoichiro Hamada, Kobe; Akira Yamashita; Keizo Ito, both of Osaka; Goro Tsukamoto, Toyonaka, all of Japan

[73] Assignee: Kanebo, Ltd., Tokyo, Japan

[21] Appl. No.: 883,118

[22] Filed: Jul. 8, 1986

[30] Foreign Application Priority Data

Jul. 16, 1985 [JP] Japan ................................ 60-157300

[51] Int. Cl.⁴ .................. A61K 31/395; C07D 295/00
[52] U.S. Cl. .................................... 514/255; 544/358; 544/403
[58] Field of Search ................ 544/403, 358; 514/255

[56] References Cited

U.S. PATENT DOCUMENTS 3,448,108  6/1969  Villani ................................. 544/403
3,738,986  6/1973  Sandler et al. ...................... 544/403
4,104,383  8/1978  Krausz ................................. 544/403

FOREIGN PATENT DOCUMENTS 1537552  9/1967  France ................................ 544/403

OTHER PUBLICATIONS

Physicians' Desk Reference, 40 Edition, 1986, pp. 614, 1110.

Primary Examiner—Donald G. Daus
Assistant Examiner—Cecilia Shen
Attorney, Agent, or Firm—Wegner & Bretschneider

[57] ABSTRACT

Novel benzylpiperazine compound of the formula:

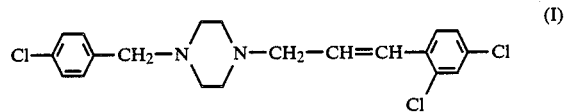

or a pharmaceutically acceptable acid addition salt thereof, which has excellent hypolipidemic activity without undesirable side effect, and a pharmaceutical composition containing the compound as an active ingredient suitable for the prophylaxis and treatment of hyperlipidemia.

3 Claims, No Drawings

BENZYLPIPERAZINE COMPOUND AND PHARMACEUTICAL COMPOSITION AS HYPOLIPIDEMIC AGENT

This invention relates to a novel benzylpiperazine compound and a pharmaceutical composition containing the same as an active ingredient. More particularly, it relates to 1-(4-chlorobenzyl) 4-(2,4-dichlorocinnamyl)piperazine of the formula:

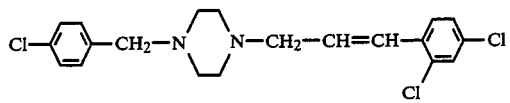

(I)

or a pharmaceutically acceptable acid addition salt thereof, and a pharmaceutical composition containing the compound as an active ingredient which is suitable for the prophylaxis and treatment of hyperlipidemia.

TECHNICAL BACKGROUND AND PRIOR ART

It is known that hyperlipidemia is a disease showing symptom of too high blood level of cholesterol and includes clinically some fundamental diseases such as chololithiasis, acute pancreatitis, xanthoma, etc. According to the recent epidemiological research, the hyperlipidemia has close relation with the appearance of arteriosclerosis, particularly atherosclerosis, and development thereof, and hence, this disease is one of the most important danger signal of ischemis heart diseases (e.g. angina pectoris, myocardial infarction) and cerebral infarction. From these viewpoints, it has been desired to find an excellent drug for the treatment of hyperlipidemia. The hypolipidemic drug is usually administered for a long period of time, and hence, the drug should be able to be administered easily (in smaller dose and in less administration time) and should exhibit the desired effect without undesirable side effect.

As a hypolipidemic drug, there have been clinically used or proposed various lipid metabolism improving drugs and cholesterol lowering drugs, such as clofibrate (chemical name: ethyl p-chlorophenoxyisobutyrate), nicotinic acid derivatives, anabolic steroids, phytosterols, anion exchange resins, and the like. However, these drugs are not necessarily satisfactory. For instance, although clofibrate has clinically widely been used, it shows less cholesterol lowering activity and has a problem of side effect, particularly hepatic toxicity (cf. J. K. Reddy et al., Nature, Vol. 283, 397–398, 1980). There has also been developed probucol of the formula:

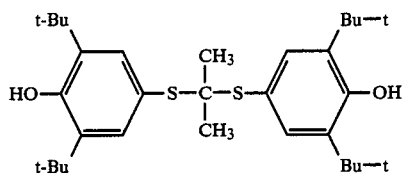

wherein t-Bu means tert-butyl, but this drug is still unsatisfactory.

SUMMARY OF THE INVENTION

The present inventors have intensively studied on improved hypolipidemic drug which has excellent activity without side effect and have found that the novel benzylpiperazine compound of the above formula (I) has the desired hypolipidemic activity.

An object of the invention is to provide a novel compound having excellent activity for lowering lipids, particularly cholesterol, in blood. Another object of the invention is to provide an improved hypolipidemic drug having excellent hypolipidemic activity without side effect, particularly hepatic toxicity. These and other objects and advantages of the invention will be apparent to skilled persons from the following description.

DETAILED DESCRIPTION OF THE INVENTION

The novel compound of this invention is 1-(4-chlorobenzyl)-4-(2,4-dichlorocinnamyl)piperazine of the formula (I) and a pharmaceutically acceptable acid addition salt thereof.

The pharmaceutically acceptable acid addition salt includes inorganic acid addition salts, such as hydrochloride, hydrobromide, sulfate, etc. and organic acid addition salts, such as maleate, fumarate, succinate, citrate, etc.

The compound (I) of this invention can be prepared by various processes, preferably by the following three processes (Process A, Process B and Process C).

Process A is illustrated by the following reaction scheme.

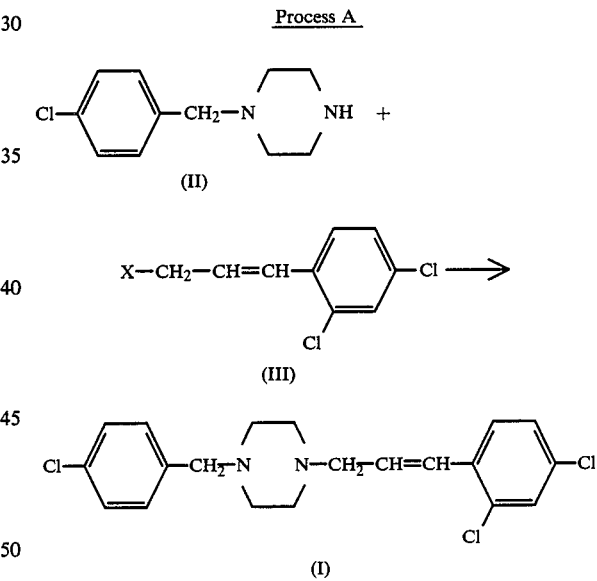

wherein X is a halogen atom, such as chlorine, bromine or iodine.

That is, the compound (I) of this invention can be prepared by reacting N-(4-chlorobenzyl)piperazine (II) or a salt thereof with a 2,4-dichlorocinnamyl halide (III). The starting compound (II) and compound (III) wherein X is chlorine are known, and the compound (III) wherein X is bromine or iodine can be prepared from known 2,4-dichlorocinnamyl alcohol by a known process.

The reaction of the compound (II) and the compound (III) can be carried out by reacting the compound (II) or a salt thereof with equimolar or slightly excess amount of the compound (III) in a solvent in the presence of a base (e.g. triethylamine) at a temperature from 50° C. to a boiling point of the solvent. Suitable solvent is inert solvents, such as benzene, toluene, xylene, and the reaction time is usually 1 to 10 hours.

Process B is illustrated by the following reaction scheme.

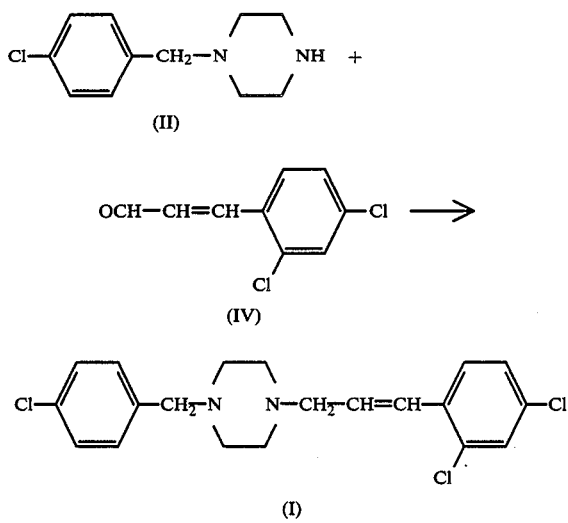

That is, the compound (I) can be prepared by reacting the known N-(4-chlorobenzyl)piperazine (II) and the known 2,4-dichlorocinnamaldehyde (IV).

This reaction may be carried out under various conditions, but preferably by melting the piperazine derivative (II) and the cinnamaldehyde derivative (IV) with heating without using any solvent, followed by adding thereto formic acid to effect reductive condensation reaction. The cinnamaldehyde (IV) is preferably used in an amount of equimolar or slightly excess to that of the piperazine derivative (II), and the formic acid is preferably used in an amount of 1 to 3 folds as much as the amount of the piperazine derivative (II). The reaction temperature is preferably in the range of 100° to 150° C. and the reaction time is usually 30 minutes to 2 hours.

Process C is illustrated by the following reaction scheme.

mixture to reduction reaction at 0° C. to room temperature.

The starting compound (V) is a novel compound and can be prepared by reacting a known 2,4-dichlorocinnamic acid or a reactive derivative thereof and N-(4-chlorobenzyl)piperazine (II) by a conventional method.

The compound (I) obtained by the above processes is preferably isolated from the reaction mixture in the form of an acid addition salt thereof as mentioned hereinbefore, and if necessary, it is converted into a free base or in turn to other various acid addition salts by a conventional method.

The compound (I) of this invention has potent activity of lowering cholesterol in blood without side effect as is described hereinafter, and hence, is useful as a hypolipidemic drug.

The compound of this invention is administered to patient as a hypolipidemic drug by oral or parenteral route, preferably by oral route. The compound, particularly a pharmaceutically acceptable acid addition salt thereof, is preferably used in the form of a pharmaceutical preparation suitable for oral administration in admixture with conventional pharmaceutically acceptable carrier or diluent, for example, excipients (e.g. lactose, synthetic aluminum silicate, glucose, mannitol, etc.), disintegrators (e.g. carboxymethyl cellulose, sodium arginate, etc.), lubricants (e.g. magnesium stearate, talc, etc.), binding agents (e.g. corn starch, polyvinylpyrrolidone, etc.). The preparations may be tablets, granules, powders, or capsules wherein granules or powders are contained.

Dose of the compound (I) is usually in the range of 1 to 100 mg/kg/day in adult in case of oral administration, which may be administered at one time or may be divided into two or three times.

The hypolipedimic activity of the compound (I) of this invention is demonstrated by (1) blood cholesterol lowering activity in rats fed with normal feed (cf. A. V. Ginocchio et al., Arzneim.-Forsch./Drug Res., Vol. 30, 2032-2034, 1980), (2) blood cholesterol lowering activity in mice fed with normal feed (cf. H. B. Wright et al., J. Med. Chem., Vol. 7, 113-115, 1964), and (3) blood cholesterol lowering activity in hypercholesterolemic mice (cf. H. Ozawa, Screening of Pharmaceutical Activities for Development of New Drugs-Recent Movement and Practice, Vol. 1, 84-86, 1984 issued by Seishi Shoin, Tokyo).

It was experimentally proved that the compound of this invention has higher activities than those of probu-

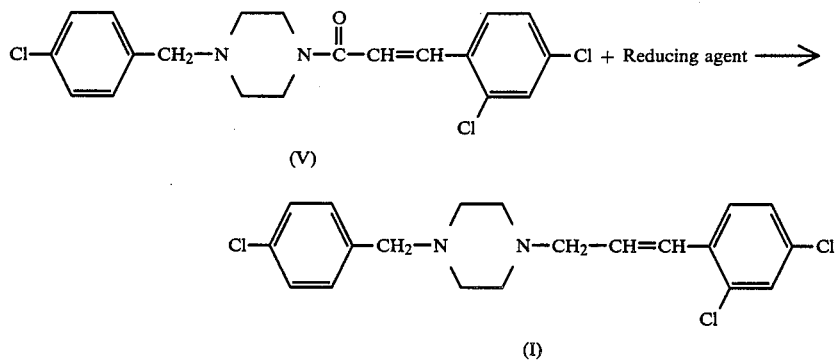

That is, the compound (I) can be prepared by suspending or dissolving the compound (V) in a solvent (e.g. diethyl ether, tetrahydrofuran, etc.), adding thereto a slightly excess amount of a reducing agent (e.g. lithium aluminum hydride, etc.) and subjecting the col in all experiments (cf. Experiments 1 to 3 hereinafter).

The side effect of hepatic toxicity was studied in the index of change of weight of liver (cf. E. R. Wagner et al., J. Med. Chem., Vol. 20, 1007–1013, 1977). As a result, the compound of this invention did not give any effect on the weight of liver, which means that the compound has no hepatic toxicity (cf. Experiments 4 to 5 hereinafter).

Moreover, the compound of this invention has low acute toxicity (cf. Experiment 6 hereinafter).

Thus, the compound of this invention is useful as a hypolipidemic drug with high safety for the prophylaxis and treatment of hyperlipidemia.

EXPERIMENT 1

Blood cholestrol lowering activity in rats fed with normal feed:

(1) Test compounds:

1-(4-Chlorobenzyl)-4-(2,4-dichlorocinnamyl)-piperazine dihydrochloride (compound of this invention)

Probucol (reference compound)

(2) Test method:

It was done by a method similar to that of A. V. Ginocchio et al. (cf. A. V. Ginocchio et al., Arzneim.-Forsch./Drug Res., Vol. 30, 2032–2034, 1980).

Wistar male rats (weighing 100–130 g, one group: 6 rats) were administered with a suspension of the test compound in 3 w/v % aqueous gum arabic solution once a day for 7 days. 24 hours after the final administration of the test compound, under light anesthesia with ether, the femoral artery and vein were cut and blood was collected therefrom. The blood was centrifuged at 3,000 r.p.m. for 10 minutes to collect serum. The serum cholesterol was measured by an enzymatic method using an agent for measuring total cholesterol (Determiner ® TC "5", manufactured by Kyowa Medex Co., Ltd.) (cf. Charles C. Allain et al., Clin. Chem., Vol. 20, 470–475, 1974).

From the data thus obtained, a mean value (X) of the serum cholesterol level in the group to which no test compound was administered and a mean value (Y) of the serum cholesterol level in the group to which the test compound was administered were calculated, and the significant difference between them was tested (t-test). From the resulting data, the percentage change of serum cholesterol in the test compound-administering group was calculated by the following equation.

$$\text{Percentage change of serum cholesterol (\%)} = \frac{Y - X}{X} \times 100$$

(3) The results are shown in Table 1.

TABLE 1

| Test compd. | Dose per once (mg/kg) | Serum cholesterol level (mg/dl) mean ± S.E. | Percentage change of serum cholesterol (%) |
|---|---|---|---|
| — | 0 | 70.9 ± 0.9 | — |
| Compound of this invention | 12.5 | 67.1 ± 2.1 | −5.4 |
|  | 25 | 62.8 ± 0.8*** | −11.4 |
|  | 50 | 64.4 ± 1.6** | −9.2 |
|  | 100 | 44.6 ± 2.1*** | −37.1 |
| Reference compound | 100 | 70.8 ± 2.0 | −0.1 |

(p < 0.01, and *p < 0.001)

As is clear from the above results, the compound of this invention showed more potent serum cholesterol lowering activity in comparison with the known probucol.

EXPERIMENT 2

Blood cholesterol lowering activity in mice fed with normal feed:

(1) Test compounds:

The same as in Experiment 1

(2) Test method:

It was done by a method similar to that of H. B. Right et al. (cf. H. B. Right et al., J. Med. Chem., Vol. 7, 113–115, 1964).

ddY male mice (weighing 21–23 g, one group: 10 mice) were fed with a mixture of the test compound with powdery feed CE-2 (manufactured by CLEA JAPAN INC.) for 7 days. When the mice fed with the feed mixed with the test compound (test compound-administering group) and the mice fed with the feed mixed with no test compound (no test compound-administering group) were compared as to the feed uptake amount and body weight, there was observed no difference between two groups. After feeding for 7 days, under light anesthesia with ether, the femoral artery and vein were cut and blood was collected therefrom. The blood was centrifuged at 3,000 r.p.m. for 10 minutes to collect serum. The serum cholesterol was measured in the same manner as described in Experiment 1.

From the data thus obtained, a mean value (X) of the serum cholesterol level in the no test compound-administering group and a mean value (Y) of the serum cholesterol level in the test compound-administering group were calculated, and the significant difference between them was tested (t-test). From the resulting data, the percentage change of serum cholesterol in the test compound-administering group was calculated by the following equation.

$$\text{Percentage change of serum cholesterol (\%)} = \frac{Y - X}{X} \times 100$$

(3) The results are shown in Table 2.

TABLE 2

| Test compd. | Conc. of test compd. in feeds (%) | Serum cholesterol level (mg/dl) mean ± S.E. | Percentage change of serum cholesterol (%) |
|---|---|---|---|
| — | 0 | 150.2 ± 3.8 | — |
| Compound of this invention | 0.0125 | 130.7 ± 6.5* | −13.0 |
|  | 0.025 | 121.0 ± 3.7*** | −19.4 |
|  | 0.05 | 62.9 ± 6.4*** | −58.1 |
|  | 0.1 | 31.7 ± 3.7*** | −78.9 |
| Reference compound | 0.025 | 121.7 ± 3.1*** | −19.0 |
|  | 0.05 | 104.8 ± 4.4*** | −30.2 |
|  | 0.1 | 84.4 ± 5.4*** | −43.8 |

(*p < 0.05, and ***p < 0.001)

As is clear from the above results, the compound of this invention showed more potent serum cholesterol lowering activity in comparison with the known probucol.

EXPERIMENT 3

Blood cholesterol lowering activity in hypercholesterolemic mice:

(1) Test compounds:

The same as in Experiment 1

(2) Test method:

It was done by a method similar to that described in H. Ozawa, Screening of Pharmaceutical Activities for Development of New Drugs - Recent Movement and Practice, Vol. 1, 84–86, 1984 issued by Seishi Shoin (Tokyo).

ddY male mice (weighing 10 - 12 g, one group: 10 mice) were fed with hypercholesterol feed [prepared by mixing CE-2 Feed (manufactured by CLEA JAPAN INC.) with cholesterol 1 w/w %, cholic acid 0.5 w/w % and sucrose 10 w/w %]. After 7 days from the starting of feeding with the hypercholesterol feed, and thereafter 6 hours and further 24 hours (totally three times), a suspension of the test compound in 3 w/v % aqueous gum arabic solution was orally administered. 3 hours after the final administration of the test compound, blood was collected from orbital vessel with hematocrit capillary (manufactured by TERUMO Corporation, treated with heparin). The blood was centrifuged at 10,000 r.p.m. for 2 minutes to collect blood plasma. The plasma cholesterol was measured in the same manner as described in Experiment 1.

From the data thus obtained, a mean value (X) of the plasma cholesterol level in the no test compound-administering group and a mean value (Y) of the plasma cholesterol level in the test compound-administering group were calculated, and the significant difference between them was tested (t-test). From the resulting data, the percentage change of plasma cholesterol in the test compound-administering group was calculated by the following equation.

$$\text{Percentage change of plasma cholesterol (\%)} = \frac{Y-X}{X} \times 100$$

(3) The results are shown in Table 3.

TABLE 3

| Test compd. | Dose per once (mg/kg) | Plasma cholesterol level (mg/dl) mean ± S.E. | Percentage change of plasma cholesterol (%) |
|---|---|---|---|
| — | 0 | 445.8 ± 34.5 | — |
| Compound of this invention | 25 | 313.1 ± 26.0** | −29.8 |
| | 50 | 314.5 ± 16.3** | −29.5 |
| | 100 | 256.0 ± 19.4*** | −42.6 |
| Reference compound | 100 | 386.2 ± 10.5 | −13.4 |

(p < 0.01., and *p < 0.001)

As is clear from the above results, the compound of this invention showed more potent plasma cholesterol lowering activity in comparison with the known probucol.

EXPERIMENT 4

Test of hepatic toxicity in rats:
(1) Test compounds:
The same as in Experiment 1
(2) Test method:
Wistar male rats (weighing 100–130 g, one group: rats) were orally administered with a suspension of the test compound in 3 w/v % aqueous gum arabic solution once a day for 7 days. 24 hours after the final administration of the test compound, under light anesthesia with ether, the liver was taken out and the weight thereof was measured.

From the data thus obtained, a mean value (X) of the weight of liver in the no test compound-administering group and a mean value (Y) of the weight of liver in the test compound-administering group were calculated, and the significant difference between them was tested (t-test). From the resulting data, the percentage change of weight of liver in the test compound-administering group was calculated by the following equation.

$$\text{Percentage change of weight of liver (\%)} = \frac{Y-X}{X} \times 100$$

(3) The results are shown in Table 4.

TABLE 4

| Test compd. | Dose per once (mg/kg) | Weight of liver (g/100 g of body weight) mean ± S.E. | Percentage change of weight of liver (%) |
|---|---|---|---|
| — | 0 | 4.91 ± 0.14 | — |
| Compound of this invention | 12.5 | 4.77 ± 0.07 | −2.9 |
| | 25 | 4.93 ± 0.10 | +0.4 |
| | 50 | 5.05 ± 0.08 | +2.9 |
| | 100 | 5.17 ± 0.07 | +5.3 |
| Reference compound | 100 | 4.68 ± 0.09 | −4.7 |

As is clear from the above results, the administration of the compound of this invention did not give any significant change in the weight of liver.

EXPERIMENT 5

Test of hepatic toxicity in mice:
(1) Test compounds:
The same as in Experiment 1
(2) Test method:
ddY male mice (weighing 21–23 g, one group: 10 mice) were fed with a mixture of the test compound with powdery feed CE-2 (manufactured by CLEA JAPAN INC.) for 7 days. When the mice fed with the feed mixed with the test compound (test compound-administering group) and the mice fed with the feed mixed with no test compound (no test compound-administering group) were compared as to the feed uptake amount and body weight, there was observed no difference between two groups. After feeding for 7 days, under light anesthesia with ether, the liver was taken out, and the weight thereof was measured.

From the data thus obtained, a mean value (X) of the weight of liver in the no test compound-administering group and a mean value (Y) of the weight of liver in the test compound-administering group were calculated, and the significant difference between them was tested (t-test). From the resulting data, the percentage change of weight of liver in the test compound-administering group was calculated by the following equation.

$$\text{Percentage change of weight of liver (\%)} = \frac{Y-X}{X} \times 100$$

(3) The results are shown in Table 5.

TABLE 5

| Test compd. | Conc. of test compd. in feeds (%) | Weight of liver (g/100 g of body weight) mean ± S.E. | Percentage change of weight of liver (%) |
|---|---|---|---|
| — | 0 | 6.35 ± 0.17 | — |
| Compound of this invention | 0.0125 | 6.80 ± 0.22 | +7.1 |
| | 0.025 | 6.63 ± 0.22 | +4.4 |
| | 0.05 | 6.86 ± 0.30 | +8.0 |
| | 0.1 | 6.43 ± 0.42 | +1.3 |
| Reference compound | 0.025 | 6.66 ± 0.22 | +4.9 |
| | 0.05 | 7.11 ± 0.13** | +12.0 |

TABLE 5-continued

| Test compd. | Conc. of test compd. in feeds (%) | Weight of liver (g/100 g of body weight mean ± S.E. | Percentage change of weight of liver (%) |
|---|---|---|---|
| | 0.1 | 7.03 ± 0.09* | +10.7 |

(*p < 0.05, and **p < 0.01)

As is clear from the above results, the administration of the compound of this invention did not give any significant change in the weight of liver.

EXPERIMENT 6

Test of acute toxicity ($LD_{50}$):
(1) Test compounds:
The same as in Experiment 1
(2) Test method:
ddY male mice (weighing 20-25 g, one group: 5 mice) were orally administered with a suspension of the test compound in 3 w/v % aqueous gum arabic solution. The death of mice was observed for 7 days, and the acute toxicity ($LD_{50}$) was calculated by Weil method.
(3) The results are shown in Table 6.

TABLE 6

| Test Compound | $LD_{50}$ (mg/kg) |
|---|---|
| Compound of this invention | 996 |
| Reference compound | >5000 |

Thus, the compound of this invention has low acute toxicity.

According to the above experiments, it is clear that the compound of this invention shows excellent hypolipidemic activity with low toxicity and hence is useful as a drug for the prophylaxis and treatment of hyperlipidemia.

The preparation of the compound and the pharmaceutical composition of this invention are illustrated by the following Reference Example, Examples and Preparations.

REFERENCE EXAMPLE 1

Preparation of 1-(4-chlorobenzyl)-4-(2,4-dichloroinnamoyl)piperazine [compound of the formula (V)]

In a mixture of acetonitrile and tert-butanol (5:1, v/v, 20 ml) are dissolved 2,4-dichlorocinnamic acid (4.3 g, 19.8 mmole) and triethylamine (3 ml, 21.5 mmole), and the mixture is cooled with an ice water bath. To the mixture is added dropwise a solution of ethyl chloroformate (2 ml, 21.0 mmole) in a mixture of acetonitrile and tert-butanol (5:1, v/v, 5 ml) over a period of 3 minutes. After the addition, the mixture is stirred for 5 minutes, and then to the mixture is added an aqueous solution (15 ml) of N-(4-chlorobenzyl)piperazine (4.2 g, 20 mmole) (which is prepared by the process as disclosed in Yoshiaki Ikeda et al., Yakugaku Zasshi, Vol. 89, 669-676, 1969), and the mixture is stirred at room temperature for 30 minutes. The reaction mixture is concentrated under reduced pressure until about half volume, and thereto is added water (20 ml), and then extracted with benzene (30 ml) twice. The organic layer is washed with water, dried over anhydrous magnesium sulfate, and concentrated to dryness. The resulting residue is recrystallized from methanol to give 1-(4-chlorobenzyl)-4-(2,4-dichlorocinnamoyl)piperazine (5.3 g, 65 %) as yellow crystals.

M.p. 104°-106° C.
NMR (CDCl$_3$)δ: 2.3-2.7 (4H, m), 3.3-3.9 (4H, m), 3.47 (2H, s), 6.74 (1H, d, J=16 Hz), 7.0-7.6 (7H, m), 7.8 (1H, d, J=16 Hz).
Elementary analysis for C$_{20}$H$_{19}$Cl$_3$N$_2$O:
Calcd. (%): C,58.62: H,4.67: N,6.84. Found (%): C,58.74; H,4.54; N,7.02.

EXAMPLE 1

Preparation of 1-(4-chlorobenzyl)-4-(2,4-dichlorocinnamyl)piperazine and salts thereof (preparation by Process A)

N-(4-Chlorobenzyl)piperazine (2.1 g, 9.98 mmole) (which is prepared by the process as disclosed in Yoshiaki Ikeda et al., Yakugaku Zasshi, Vol. 89, 669-676, 1969), 2,4-dichlorocinnamyl chloride (2.3 g, 10.38 mmole) (which is prepared by the process as disclosed in G. Cignerella et al., J. Med. Chem., Vol. 8, 326-331, 1965) and triethylamine (1.5 g, 14.82 mmole) are added to benzene (50 ml), and the mixture is refluxed for 3 hours. The reaction mixture is allowed to cool to room temperature, and thereto are added water and ethyl acetate. The organic layer is separated, dried over anhydrous magnesium sulfate, and then the solvent is distilled off to give a crude product (free base) as an oily substance. From the oily substance, 1-(4-chlorobenzyl)-4-(2,4-dichlorocinnamyl)piperazine and acid addition salts thereof are obtained in the following manner.

(1) Dihydrochloride:
The oily substance is dissolved in ethanol (5 ml) and thereto is added an ethanol solution (40 ml) of conc. hydrochloric acid (2.0 ml), and the precipitated crystals are collected by filtration. The crystals are recrystallized from water-ethanol to give 1-(4-chlorobenzyl)-4-(2,4-dichlorocinnamyl)piperazine dihydrochloride (1.8 g, 38 %) as colorless crystals.
M.p. 270°-275° C. (decomp.).
NMR (CF$_3$COOH)δ: 3.5-4.4 (10H, m), 4.4-4.8 (2H, broad s), 6.0-6.8 (1H, m), 7.0-7.8 (8H, m).
Elementary analysis for C$_{20}$H$_{21}$Cl$_3$N$_2$.2HCl: Calcd. (%): C,51.25; H,4.95: N,5.98. Found (%): C,51.30: H,4.83: N,6.06.

In the same manner as described above except that maleic acid or fumaric acid is used instead of hydrochloric acid, there are prepared the corresponding acid addition salts. The physical properties of these compounds are shown below.

(2) Dimaleate:
Appearance: Colorless crystals
M.p. 182°-187° C. (decomp.)
NMR (DMSO-d$_6$)δ: 2.3-3.5 (8H, m), 3.5-4.1 (4H, m), 6.2 (4H, s), 6.0-8.0 (9H, m).
Elementary analysis for C$_{20}$H$_{21}$Cl$_3$N$_2$.2C$_4$H$_4$O$_4$:
Calcd. (%): C,53.56: H,4.66: N,4.46. Found (%): C,53.52: H,4.69: N,4.54.

(3) Difumarate:
Appearance: Colorless crystals
M.p. 202°-206° C. (decomp.)
NMR (DMSO-d$_6$)δ: 2.3-3.0 (8H, m), 3.4 (2H, d, J=6 Hz), 3.6 (2H, s), 6.67 (4H, s), 6.2-7.9 (9H, m).
Elementary analysis for C$_{20}$H$_{21}$Cl$_3$N$_2$.2C$_4$H$_4$O$_4$:
Calcd. (%): C,53.56: H,4.66: N,4.46. Found (%): C,53.58; H,4.67; N,4.56.

(4) Free base:
1-(4-Chlorobenzyl)-4-(2,4-dichlorocinnamyl)-piperazine dihydrochloride (5 g, 10.6 mmole) obtained above is added to a mixture of 10% aqueous sodium hydroxide (20 ml) and ethyl acetate (50 ml), and the mixture is stirred. The ethyl acetate layer is separated, washed with water, dried over anhydorus magnesium sulfate, and then the solvent is distilled off. The resulting oily substance of the desired free base is allowed to stand at room temperature and thereby solidified. This product is recrystallized from acetone to give 1 (4-chlorobenzyl)-4-(2,4-dichlorocinnamyl)-piperazine (2.0 g) as pale yellow crystals.

M.p. 92°–94° C.

NMR (CDCl$_3$)δ: 2.5 (8H, broad s , 3.2 (2H, d, J=6 Hz), 3.47 (2H, s), 6.3 (1H, dt, J=16 Hz, J=6 Hz), 6.87 (1H, d, J=16 Hz), 7.0–7.7 (7H, m).

Elementary analysis for $C_{20}H_{21}Cl_3N_2$: Calcd. (%): C,60.70: H,5.35: N,7.08. Found (%): C,60.76: H,5.25: N,7.13.

EXAMPLE 2

Preparation of 1-(4-chlorobenzyl)-4-(2,4-dichlorocinnamyl)piperazine dihydrochloride (preparation by Process B)

N-(4-Chlorobenzyl)piperazine (4.2 g, 19.93 mmole) (which is prepared by the process as disclosed in Yoshiaki Ikeda et al., Yakugaku Zasshi, Vol. 89, 669–676, 1969) and 2,4-dichlorocinnamaldehyde (4.1 g, 20.39 mmole) (which is prepared by the process as disclosed in U.S. Pat. No. 3,094,561) are mixed and heated on an oil bath at 130° C. to melt them, and thereto is added dropwise formic acid (2.0 ml, 52.6 mmole), and the mixture is stirred under heating for 30 minutes. The reaction mixture is allowed to cool and is dissolved in ethanol (30 ml), and to the solution is added an ethanol solution (90 ml) of conc. hydrochloric acid (4.5 ml). The precipitated crystals are separated by filtration. The crystals are recrystallized from water-ethanol to give the title compound (3.8 g). The product shows the same physical properties as those of the compound prepared in Example 1-(1).

EXAMPLE 3

Preparation of 1-(4-chlorobenzyl)-4-(2,4-dichlorocinnamyl)piperazine dihydrochloride (preparation by Process C)

1-(4-Chlorobenzyl)-4-(2,4-dichlorocinnamoyl)piperazine (1.0 g, 2.44 mmole) (the compound prepared in Reference Example 1) is dissolved in anhydrous tetrahydrofuran (10 ml), and thereto is added in portions lithium aluminum hydride (0.1 g, 2.63 mmole) at room temperature. After the addition, the mixture is stirred at room temperature for one hour. After adding water in portions, the reaction mixture is neutralized to approximately neutral with 3N hydrochloric acid, and then is extracted with ethyl acetate. The ethyl acetate layer is separated, washed with water, dried over anhydrous magnesium sulfate, and then the solvent is distilled off. The resulting oily substance is dissolved in ethanol (5 ml), and thereto is added an ethanol solution (10 ml) of conc. hydrochloric acid (0.5 ml), and the precipitated crystals are separated by filtration. The product is recrystallized from water-ethanol to give the title compound (0.2 g). The product has the same physical properties as those of the compound prepared in Example 1-(1).

EXAMPLE 4

Preparation of tablets:
[Formulation]:

| Components | Amount |
| --- | --- |
| The compound of this invention (2HCl) | 250 parts by weight |
| Lactose | 76 parts by weight |
| Corn starch | 50 parts by weight |
| Crystalline cellulose | 20 parts by weight |
| Magnesium stearate | 4 parts by weight |

The compound of this invention (2HCl), lactose and crystalline cellulose are mixed homogeneously, and to the powdery mixture is added 5% aqueous corn starch solution in an amount of about ¼ of that of the mixture, and the mixture is granulated by a wet granulation process. To the granules thus prepared are added remaining corn starch and magnesium stearate, and the mixture is tabletted to prepare tablets (one tablet: 400 mg, the content of the compound of this invention (2HCl): 250 mg per each tablet).

EXAMPLE 5

Preparation of capsules:
[Formulation]:

| Components | Amount |
| --- | --- |
| The compound of this invention (2HCl) | 250 parts by weight |
| Corn starch | 47 parts by weight |
| Magnesium stearate | 3 parts by weight |

[Procedure]:

The above components are mixed homogeneously, and the powdery mixture is packed in capsules in an amount of each 300 mg to prepare capsules (the content of the compound of this invention (2HCl): 250 mg per each capsule).

EXAMPLE 6

Preparation of granules:
[Formulation]:

| Components | Amount |
| --- | --- |
| The compound of this invention (2HCl) | 250 parts by weight |
| Lactose | 76 parts by weight |
| Corn starch | 4 parts by weight |

[Procedure]:

The compound of this invention (2HCl), lactose and corn starch are dissolved in water to prepare 5 % aqueous solution, and the mixture is granulated by a wet granulation process to give granules (the content of the compound of this invention (2HCl): 250 mg in 330 mg granules).

What is claimed is:

1. A benzylpiperazine compound of the formula:

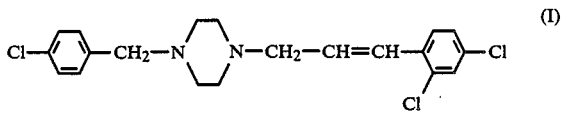

(I)

or a pharmaceutically acceptable acid addition salt thereof.

2. A pharmaceutical composition for the prophylaxis and treatment of hyperlipidemia, which comprises as an active ingredient a prophylactically or therapeutically effective amount of a compound of the formula:

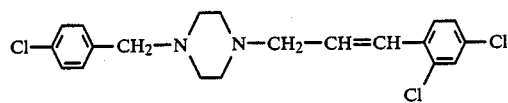

or a pharmaceutically acceptable acid addition salt thereof in admixture with a conventional pharmaceutically acceptable carrier or diluent.

3. A method for the prophylaxis and treatment of hyperlipidemia, which comprises administering a prophylactically or therapeutically effective amount of a compound of the formula:

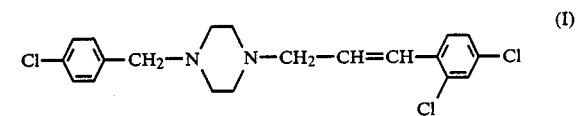

or a pharmaceutically acceptable acid addition salt thereof to a patient.

* * * * *